United States Patent [19]

Folland

[11] 4,241,290
[45] Dec. 23, 1980

[54] CLINICAL MIRROR HEATING DEVICE

[76] Inventor: Roy E. Folland, R.R. 1 S. Beech Ridge Rd., Clarenceville, Quebec, Canada

[21] Appl. No.: 949,258

[22] Filed: Oct. 6, 1978

[51] Int. Cl.$^3$ .......................... H05B 1/02; H01H 3/16; F26B 19/00

[52] U.S. Cl. .................................... 219/518; 34/202; 200/61.59; 219/219; 219/242; 219/521; 350/61

[58] Field of Search ..................... 200/61.59, 61.58, 85; 219/219, 242, 521, 520, 518, 385, 386; 34/202, 239; 350/61; 99/389, 391, 392

[56] References Cited

U.S. PATENT DOCUMENTS

| | | | |
|---|---|---|---|
| 1,184,949 | 5/1916 | Gwynn | 219/521 X |
| 1,417,079 | 5/1922 | Lebzelter | 219/521 X |
| 1,604,972 | 11/1926 | Clarke | 219/521 |
| 2,025,899 | 12/1935 | Rhodes | 219/385 X |
| 2,093,059 | 9/1937 | Schröder | 34/239 |
| 2,262,506 | 11/1941 | Levandowski | 219/521 |
| 2,527,049 | 10/1950 | Aagesen | 219/385 |
| 2,555,416 | 6/1951 | Marano | 219/521 |
| 2,682,829 | 7/1954 | Kouvallis | 99/389 |
| 2,831,096 | 4/1958 | Signore | 219/521 UX |
| 3,703,634 | 11/1972 | Bucky | 219/521 X |
| 3,723,704 | 3/1973 | Silverthorne | 219/242 |
| 3,816,705 | 6/1974 | Ebert | 219/521 |

Primary Examiner—A. Bartis

Attorney, Agent, or Firm—Alan Swabey; Robert E. Mitchell; Guy J. Houle

[57] ABSTRACT

An electrical heater device for heating a clinical mirror. The device comprises a housing having a top, bottom and side walls to define a hollow enclosure. Two spiral coiled electric heating elements are secured in the housing with their heat radiating surface spaced apart and facing each other in juxtaposition to provide concentrated heat in a mirror locating space therebetween. An opening is provided in the top wall in alignment with the mirror locating space through which the mirror can be inserted into the mirror locating space. A switch is positioned in alignment with the mirror locating space below the heating elements. The switch has an activating contact on an upper face thereof located in alignment with the opening in the top wall and the mirror locating space for activation by a clinical mirrow when the mirror element of such is inserted into the mirror locating space. The activating contact has a centering element shaped to position and maintain the mirror element of the clinical mirror in centered alignment between and with the heat radiating surfaces of the electric heating elements in the mirror locating space. Electrical connections are provided for connecting the heating elements and the switch to a current source for energization of the heating elements when the switch is activated by engagement of the activating contact by the mirror element of the clinical mirror inserted through the opening in the top wall.

2 Claims, 3 Drawing Figures

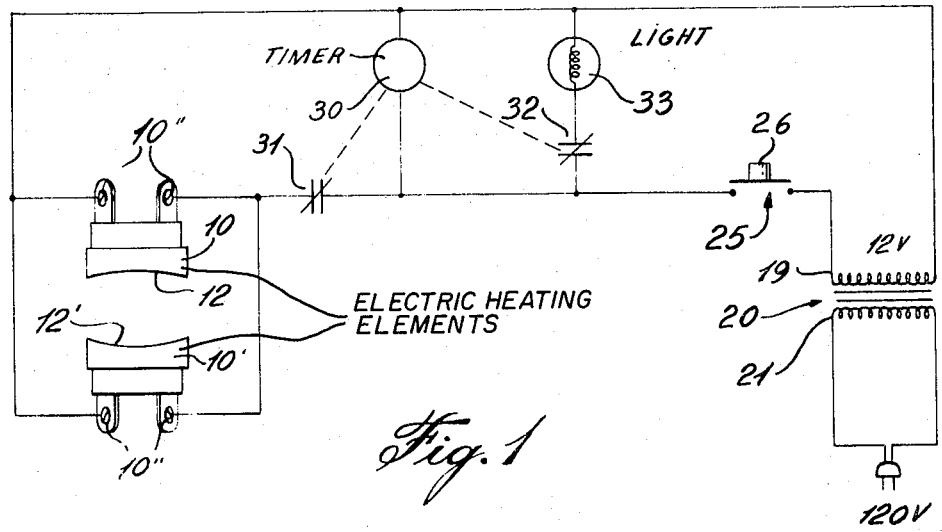
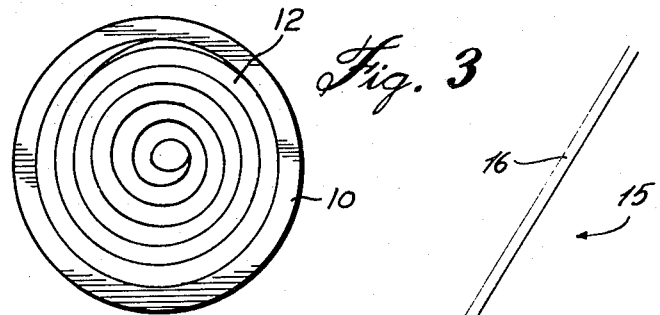
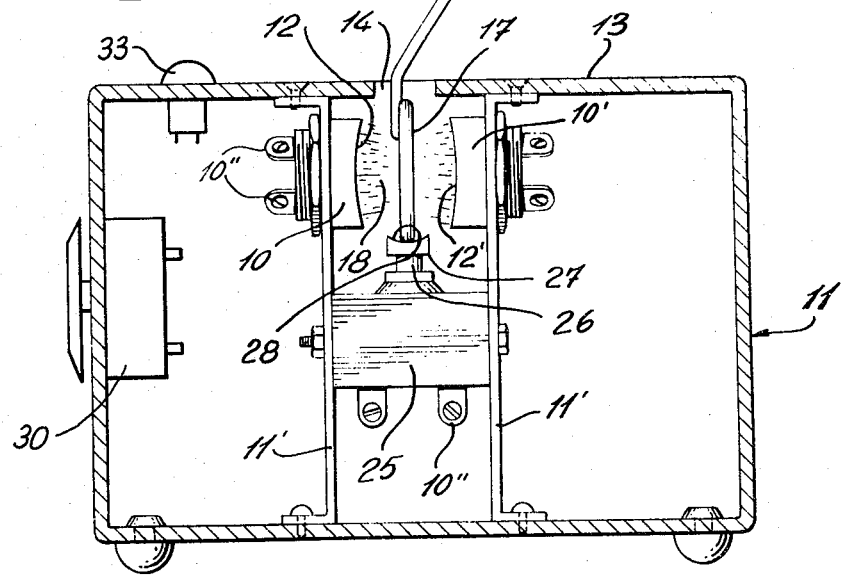

CLINICAL MIRROR HEATING DEVICE

BACKGROUND OF INVENTION (a) Field of the Invention

The present invention relates to an electrical heater device for heating a clinical mirror.

(b) Description of Prior Art

Clinical mirrors of the type comprising a mirror stem with a mirror element at one end and for use particularly in viewing areas of the mouth of patients to examine the throat area or the teeth area of the mouth, require heating to sterilize and to prevent fogging of the mirror when inserted in the mouth of the patient. A common practice, at the moment, involves heating the mirror element with an alchol burner. A disadvantage of the use of such burners is that it is dangerous to use in a doctor's office as there exists a fire hazard, and require filing, from time-to-time. This is a messy operation and a supply of oil has to be maintained. Furthermore, such burners do not release uniform heat and the mirror could be damaged thereby.

SUMMARY OF INVENTION

It is a feature of the present invention to provide an electric heater device for such use and which substantially overcomes all of the above-mentioned disadvantages.

An electrical heater device for heating a clinical mirror. The device comprises a housing having a top, bottom and side walls to define a hollow enclosure. Two spiral coiled electric heating elements are secured in the housing with their heat radiating surface spaced apart and facing each other in juxtaposition to provide concentrated heat in a mirror locating space therebetween. An opening is provided in the top wall in alignment with the mirror locating space through which the mirror can be inserted into the mirror locating space. A switch is positioned in alignment with the mirror locating space below the heating elements. The switch has an activating contact on an upper face thereof located in alignment with the opening in the top wall and the mirror locating space for activation by a clinical mirror when the mirror element of such is inserted into the mirror locating space. The activating contact has a centering element shaped to position and maintain the mirror element of the clinical mirror in centered alignment between and with the heat radiating surfaces of the electric heating elements in the mirror locating space. Electrical connections are provided for connecting the heating elements and the switch to a current source for energization of the heating elements when the switch is activated by engagement of the activating contact by the mirror element of the clinical mirror inserted through the opening in the top wall.

BRIEF DESCRIPTION OF DRAWINGS

A preferred embodiment of the present invention will now be described with reference to the example thereof illustrated by the accompanying drawings in which:

FIG. 1 is a schematic diagram showing an example of the electrical circuit for the heater device;

FIG. 2 is a section view of an example of the construction of the electrical heater device; and FIG. 3 is a plan view of a heating element.

DESCRIPTION OF PREFERRED EMBODIMENTS

Referring now to the drawings, and more particularly to FIG. 1, there is shown an example of the electric circuitry of the heater device. The device comprises one or more electric heating elements, herein two electric heating elements 10 and 10', each element having a heat radiating surface 12 and 12'. The heating elements 10 and 10' herein shown in FIG. 3 have a spiral coiled resistive heat radiating surface 12 whereby to generate concentrated heat on the mirror element 17 of a clinical mirror 15.

Referring now to FIG. 2, it can be seen that the electrical heating elements 10 and 10' are secured in a housing 11 adjacent and below the top wall 13. An opening 14 is provided in the top wall 13 and located to permit entry of a portion of the clinical mirror 15 therein. The mirror 15 has a stem 16 and a mirror element 17. As shown the heat radiating surfaces 12 and 12' of the electrical heating elements are spaced-apart and face each other in juxtaposition to define a mirror locating space 18 therebetween.

In one embodiment of the heater device the heating elements 10 and 10' are connected directly to a 12 volt D.C. battery (not shown) and switched on by means of a switch connected in the electric circuit. Also, it is foreseeable that the heating elements may be energized directly from a 120 volt A.C. voltage. In the particular embodiment of the electrical circuits shown in FIG. 1, the heating elements 10 and 10' are connected to the secondary winding 19 of the step-down transformer 20. The primary winding 21 of the transformer 20 is connected to a standard 120 volt A.C. supply.

Referring to the drawings, there is shown a switch 25 connected in the electric circuit whereby to energize the electric heating elements 10 and 10'. The switch 25 is provided with an activating contact 26 and a switch is secured in the housing with the contact in alignment with the mirror locating space 18 (see FIG. 2). The switch activating contact 26 is depressed by the mirror element 17 of the clinical mirror 15 when inserted in the opening 14 whereby to cause the heating elements 10 and 10' to energize when the mirror element is in position to heat the mirror element 17 from opposed sides thereof.

The activating contact 26 may also be provided with a centering element 27 on an upper end thereof whereby to position and maintain the mirror element 17 in a proper position spaced-apart from both heating elements 10 and 10' and to prevent the mirror element from slipping off the activating contact 26 when depressed thereby. This centering element may have a concave upper face 28 to provide the proper engagement and locating of the mirror element 17. Although not shown, the mirror element 17 is usually of circular configuration and the stem 16 is an elongated rod-like stem.

Referring again to FIG. 1, there is shown a timer device 30 secured across the secondary transformer winding 19 downstream of the switch 25. The purpose of this timer is to provide a timing cycle for the duration of the energization of the electrical heating elements 10 and 10'. For this purpose the timer 30 is provided with switch contacts 31 and 32. The switch contacts 31 are connected in series with the switch 25 and will cut off the current flow to the heating elements 10 and 10'. Switch contacts 32 are secured in series with an indicator light 33, which series connections are connected across the secondary winding of the transformer 20. When the timer 30 is activated, the indicator light 33 will energize thus indicating that the heaters are in operation. As soon as the timer reaches the end of its timing cycle, the switch contact 32 will open thus causing the light to extinguish and providing a visual indication that the heating elements are no longer energized. At the same time switch contact 31 has opened to de-energize the electrical heating elements.

As shown in FIG. 1, the electrical heating elements 10 and 10' are provided with connector posts 10" connected in parallel across the secondary winding 19 of the transformer 20. Further, the housing 11 may be constructed of any suitable material and all electrical connections are isolated from the housing 11. In the particular structure shown in FIG. 2, the heating elements 10 and 10' are secured to a respective one of two vertical walls 11' positioned parallel to one another with the opening 14 extending substantially centrally thereof. The opening 14 is a slot in the top wall 13. The switch 25 is secured across the vertical walls 11'. The timer is conveniently located in the housing and may be an automatic one-cycle timer or a multi-cycle timer adjustable by a knob which may be conveniently located on an outside wall of the housing 11. The indicator light 33 can be conveniently located in the top wall 13.

It is within the ambit of the present invention to provide any obvious modifications of the preferred embodiment described herein, provided such modifications fall within the scope of the appended claims. For example, the heating element(s) could be supported without a housing and held by other suitable support means.

I claim:

1. An electrical heater device for heating a clinical mirror, said device comprising a housing having top, bottom and side walls to define a hollow enclosure; two spiral coiled electric heating elements secured in said housing with their heat radiating surface spaced apart and facing each other in juxtaposition to provide concentrated heat in a mirror locating space therebetween, an opening in said top wall in alignment with said mirror locating space through which said mirror can be inserted into said mirror locating space, a switch positioned in alignment with said mirror locating space below said heating elements, said switch having an activating contact on an upper face thereof located in alignment with said opening in said top wall and said mirror locating space for activation by a clinical mirror when the mirror element of such is inserted into said mirror locating space, said activating contact having a centering element shaped to position and maintain the mirror element of the clinical mirror in centered alignment between and with the heat radiating surfaces of said electric heating elements in said mirror locating space, and electrical connections for connecting said heating elements and switch to a current source for energization of said heating elements when said switch is activated by engagement of the activating contact by the mirror element of the clinical mirror inserted through the opening in said top wall.

2. A heater device as claimed in claim 1, wherein a timer device is connected to said switch and is activated by activation of said activating contact for controlling the period of energization of the heating elements, and an indicator light controlled by said timer device to indicate the start and end of a timing cycle.

* * * * *